US012797278B2

(12) United States Patent
Publicover et al.

(10) Patent No.: US 12,797,278 B2

(45) Date of Patent: Nov. 17, 2026

(54) KNEE AND JOINT REHABILITATION EXERCISE DEVICE

(71) Applicant: JumpSport, Inc., Saratoga, CA (US)

(72) Inventors: Mark W. Publicover, Saratoga, CA (US); Jebodiah Burns, San Jose, CA (US); Jon Patton Hylbert, Los Gatos, CA (US)

( * ) Notice: Subject to any disclaimer, the term of this patent is extended or adjusted under 35 U.S.C. 154(b) by 0 days.

(21) Appl. No.: 18/581,295

(22) Filed: Feb. 19, 2024

(65) Prior Publication Data

US 2024/0415717 A1 Dec. 19, 2024

Related U.S. Application Data

(63) Continuation of application No. 18/461,418, filed on Sep. 5, 2023, now abandoned, which is a continuation (Continued)

(51) Int. Cl.

*A61H 1/02* (2006.01)

*A61F 5/01* (2006.01)

(Continued)

(52) U.S. Cl.

CPC .......... *A61H 1/024* (2013.01); *A61F 5/0123* (2013.01); *A63B 21/00061* (2013.01);

(Continued)

(58) Field of Classification Search

CPC ............ A61H 1/024; A61H 2201/0192; A61H 2201/1253; A61H 2201/1445; A61H 2201/1645; A61H 2201/165; A61H 2201/1676; A61H 2205/102; A63B 21/4011; A63B 21/4039; A63B 21/4047; A63B 21/00061; A63B 21/00069; A63B 21/023; A63B 21/026; A63B 21/0552; A63B 21/4005; A63B 21/4007; A63B 21/4009; A63B 21/4013; A63B 21/4021; A63B 21/0557; A63B 21/154;

(Continued)

(56) References Cited

U.S. PATENT DOCUMENTS 161,323 A * 3/1875 Brown .................. A61F 5/0123 602/16

3,502,071 A * 3/1970 Holly ....................... A61H 3/00 601/34

(Continued)

FOREIGN PATENT DOCUMENTS

DE 4400820 A1 7/1995

WO WO-2008093023 A1 * 8/2008 ............. A61F 5/024

OTHER PUBLICATIONS

WO-2008093023-A1 translated (Year: 2008).*

(Continued)

*Primary Examiner* — Alireza Nia

*Assistant Examiner* — Michael Milo

(74) *Attorney, Agent, or Firm* — Klarquist Sparkman, LLP

(57) ABSTRACT

A knee rehabilitative device permits a user to provide resistive stretching caused when the leg or other joint is extended or straightened, facilitating exercise and strengthening of the user's muscles and improved flexibility in the area of the knee or other joint area.

5 Claims, 12 Drawing Sheets

Related U.S. Application Data of application No. 18/136,726, filed on Apr. 19, 2023, now abandoned, which is a continuation of application No. 18/085,414, filed on Dec. 20, 2022, now abandoned, which is a continuation of application No. 17/885,853, filed on Aug. 11, 2022, now abandoned, which is a continuation of application No. 16/883,990, filed on May 26, 2020, now abandoned, which is a continuation of application No. 16/783,092, filed on Feb. 5, 2020, now abandoned, which is a continuation of application No. 16/656,508, filed on Oct. 17, 2019, now abandoned, which is a continuation of application No. 16/459,517, filed on Jul. 1, 2019, now abandoned, which is a continuation of application No. 16/352,772, filed on Mar. 13, 2019, now abandoned, which is a continuation of application No. 16/195,784, filed on Nov. 19, 2018, now abandoned, which is a continuation of application No. 16/017,753, filed on Jun. 25, 2018, now abandoned, which is a continuation of application No. 15/121,697, filed as application No. PCT/US2015/017610 on Feb. 25, 2015, now abandoned.

(60) Provisional application No. 61/944,488, filed on Feb. 25, 2014.

(51) Int. Cl.

| | |
|---|---|
| ***A63B 21/00*** | (2006.01) |
| ***A63B 21/02*** | (2006.01) |
| ***A63B 21/055*** | (2006.01) |
| ***A63B 22/00*** | (2006.01) |
| ***A63B 23/00*** | (2006.01) |
| ***A63B 23/04*** | (2006.01) |

(52) U.S. Cl.

CPC ...... *A63B 21/00069* (2013.01); *A63B 21/023* (2013.01); *A63B 21/026* (2013.01); *A63B 21/0552* (2013.01); *A63B 21/4011* (2015.10); *A63B 21/4039* (2015.10); *A63B 21/4047* (2015.10); *A63B 23/0494* (2013.01); *A61F 2005/0179* (2013.01); *A61H 2201/0192* (2013.01); *A61H 2201/1253* (2013.01); *A61H 2201/1445* (2013.01); *A61H 2201/1645* (2013.01); *A61H 2201/165* (2013.01); *A61H 2201/1676* (2013.01); *A61H 2205/102* (2013.01); *A63B 21/0557* (2013.01); *A63B 21/154* (2013.01); *A63B 21/157* (2013.01); *A63B 21/158* (2013.01); *A63B 21/4005* (2015.10); *A63B 21/4007* (2015.10); *A63B 21/4009* (2015.10); *A63B 21/4013* (2015.10); *A63B 21/4021* (2015.10); *A63B 2022/0094* (2013.01); *A63B 2023/006* (2013.01); *A63B 2209/02* (2013.01); *A63B 2209/10* (2013.01); *A63B 2225/09* (2013.01); *A63B 2225/093* (2013.01)

(58) Field of Classification Search

CPC . A63B 21/157; A63B 21/158; A63B 23/0494; A63B 2022/0094; A63B 2023/006; A63B 2209/02; A63B 2209/10; A63B 2225/09; A63B 2225/093; A61F 5/0123; A61F 2005/0179

USPC ........................................................... 602/16

See application file for complete search history.

(56) References Cited

U.S. PATENT DOCUMENTS

| | | | | | |
|---|---|---|---|---|---|
| 3,976,057 | A | | 8/1976 | Barclay | |
| 4,214,577 | A | | 7/1980 | Hoy | |
| 4,334,528 | A | | 6/1982 | Gauvry | |
| 4,433,679 | A | | 2/1984 | Mauldin et al. | |
| 4,466,613 | A | | 8/1984 | Reese | |
| 4,546,968 | A | | 10/1985 | Silberman | |
| 4,606,542 | A | | 8/1986 | Segal | |
| 4,643,176 | A | | 2/1987 | Mason et al. | |
| 4,776,587 | A | | 10/1988 | Carlson et al. | |
| 4,838,251 | A | * | 6/1989 | Chignon | A61F 5/0125 602/16 |
| 4,848,326 | A | | 7/1989 | Lonardo | |
| 4,848,626 | A | | 7/1989 | Waters | |
| 4,899,735 | A | | 2/1990 | Townsend et al. | |
| 4,979,737 | A | | 12/1990 | Kock | |
| 4,982,732 | A | | 1/1991 | Morris | |
| 5,007,415 | A | * | 4/1991 | Marion | A61F 5/0106 473/214 |
| 5,042,799 | A | * | 8/1991 | Stanley | A63B 21/4005 482/114 |
| 5,116,296 | A | | 5/1992 | Watkins et al. | |
| 5,117,814 | A | * | 6/1992 | Luttrell | A61H 1/0266 601/33 |
| 5,181,895 | A | | 1/1993 | Larson et al. | |
| 5,203,754 | A | | 4/1993 | Maclean | |
| 5,213,094 | A | | 5/1993 | Bonutti | |
| 5,330,417 | A | | 7/1994 | Petersen et al. | |
| 5,792,034 | A | | 8/1998 | Kozlovsky | |
| 5,865,714 | A | | 2/1999 | Marlowe | |
| 5,980,435 | A | | 11/1999 | Joutras et al. | |
| 6,117,097 | A | | 9/2000 | Ruiz | |
| 6,471,664 | B1 | | 10/2002 | Campbell et al. | |
| 6,875,135 | B2 | | 4/2005 | Tracy, Sr. | |
| 7,261,679 | B2 | | 8/2007 | Sload | |
| 7,491,186 | B2 | | 2/2009 | Zeide et al. | |
| 7,947,004 | B2 | | 5/2011 | Kazerooni et al. | |
| 8,376,918 | B2 | | 2/2013 | Itzkowitz | |
| 9,220,623 | B2 | | 12/2015 | Burns | |
| 2002/0010410 | A1 | | 1/2002 | Steponovich | |
| 2005/0101895 | A1 | * | 5/2005 | Patel | A61F 5/05841 602/16 |
| 2006/0122036 | A1 | | 6/2006 | Ferrara | |
| 2006/0135904 | A1 | * | 6/2006 | Ingimundarson | A61F 5/0123 602/26 |
| 2009/0149789 | A1 | | 6/2009 | Huang et al. | |
| 2009/0312683 | A1 | * | 12/2009 | Burns | A63B 23/0494 602/26 |
| 2010/0056970 | A1 | | 3/2010 | Nace | |
| 2010/0069798 | A1 | | 3/2010 | Cheng et al. | |
| 2010/0168627 | A1 | * | 7/2010 | Einarsson | A61F 5/0125 602/26 |
| 2011/0105969 | A1 | | 5/2011 | Nace | |
| 2015/0305895 | A1 | * | 10/2015 | Boiten | A61F 2/6607 623/26 |
| 2016/0243392 | A1 | | 8/2016 | Burns | |

OTHER PUBLICATIONS

International Search Report and Written Opinion mailed May 26, 2015 for International Application No. PCT/US2015/017610, 12 pages.

* cited by examiner

KNEE AND JOINT REHABILITATION EXERCISE DEVICE

CROSS REFERENCE TO RELATED APPLICATIONS

This application is a continuation of U.S. patent application Ser. No. 18/461,418, filed Sep. 5, 2023, which is a continuation of U.S. patent application Ser. No. 18/136,726, filed Apr. 19, 2023, now abandoned, which is a continuation of U.S. patent application Ser. No. 18/085,414, filed Dec. 20, 2022, now abandoned, which is a continuation of U.S. patent application Ser. No. 17/885,853, filed Aug. 11, 2022, now abandoned, which is a continuation of U.S. patent application Ser. No. 16/883,990, filed May 26, 2020, now abandoned, which is a continuation of U.S. patent application Ser. No. 16/783,092, filed Feb. 5, 2020, now abandoned, which is a continuation of U.S. patent application Ser. No. 16/656,508, filed Oct. 17, 2019, now abandoned, which is a continuation of U.S. patent application Ser. No. 16/459,517, filed Jul. 1, 2019, now abandoned, which is a continuation of U.S. patent application Ser. No. 16/352,772, filed Mar. 13, 2019, now abandoned, which is a continuation of U.S. patent application Ser. No. 16/195,784, filed Nov. 19, 2018, now abandoned, which is a continuation of U.S. patent application Ser. No. 16/017,753, filed Jun. 25, 2018, now abandoned, which is a continuation of U.S. patent application Ser. No. 15/121,697, filed Aug. 25, 2016, now abandoned, which was the National Stage of International Patent Application No. PCT/US2015/017610, filed Feb. 25, 2015, which claims the benefit of U.S. Provisional Application No. 61/944,488, filed Feb. 25, 2014. The prior applications are incorporated herein by reference in their entirety.

BACKGROUND

This disclosure relates to a rehabilitative knee apparatus in the field of portable leg exercise devices. With today's rigorous sports activities including football, tennis, basketball and soccer it is unfortunately a common occurrence for active people to injure their knee joint to the point where surgical treatment is required to repair the knee and areas around the knee. Chronic knee degeneration also results in the need of surgical treatment such as partial and total knee joint replacements. Other joints may also be injured and rehabilitated in a similar fashion, such as the elbow as only one example, but they are not shown in this series of embodiments. Best practices after joint surgeries include participating in physical therapy that aid in regaining range of motion and strength. To obtain passive knee extension a patient may utilize a Continuous Passive Motion (CPM) or Knee Extension Splint. There are also manual practices, such as joint mobilizations that a physical therapist will use to obtain increased passive knee extension. Post-surgical strengthening of the muscles around the knee joint, especially the quadriceps, is extremely important, but can be challenging due to pain and swelling in and around the knee joint.

Because of these injuries, it has been beneficial to provide devices that help rehabilitate the knee area after surgery. Some devices are simply leg braces that help take pressure off the knee joint while it is healing. Other devices are machines or apparatus that help strengthen the leg muscles around the knee and associated with proper knee function but their mobility is minimal.

Patents that describe leg braces that help keep the knee joint supported during or while engaged in exercise include U.S. Pat. Nos. 4,982,732, 5,116,296, 4,433,679 and 5,980,435. Patents that describe exercise apparatus for helping to rehabilitate the muscles of the leg around the knee joint include U.S. Pat. Nos. 4,546,968, 4,776,587, 4,979,737 and 5,181,895. However, these patents and other commercially available exercise devices have a deficiency in that none of them allows a person to wear a light weight inexpensive brace which has connection points attached to allow the user to releasably attach an elastic band from the area of the upper leg to the area of the lower leg, and to connect a portable assembly behind the user's knee for the elastic band to stretch over to increase the resistance factor to the muscles surrounding the knee joint. Furthermore, none of the patents or other prior art shows a leg exercise device that allows the user to easily and quickly change the resistance band location from the back of the leg to the front of the leg whereby the user can connect a portable assembly in front of the knee which the elastic band passes over to passively stretch the knee joint to a straight position.

Disclosed herein is a joint rehabilitation device comprising one or more spring members; and attaching means that secure the device on either the anterior or posterior side of a joint; wherein, when worn posteriorly, the spring member provides active resistance when the joint is extended and when worn anteriorly it pushes the knee straight into passive knee extension. The joint discussed primarily is the knee joint. However, it should be appreciated that the instant device may be utilized on other joints on a body, such as elbow joint for example. Disclosed herein is a device that utilizes elastic bands or spring members in the form of flat bars, also referred to sometimes as "flat springs", that are capable of flexing in more than one direction. These flat bars resemble a leaf spring in looks and may function similarly in that they flex and bend in more than one direction. Such springs are generally longer than they are wide and consist of one or more layers of either metal or other composition of materials that are bracketed together. Historically, traditional leaf springs were made in multiple layers and called "laminated or carriage springs", but these were more generally elliptical when two portions were in a mirror to each other to form an elliptical shape. They could also be "semi-elliptic" where only one portion was utilized in opposition to a non spring member serving as a fulcrum. Other forms can be known as "three quarter elliptic, quarter elliptic, or transverse" Leaf spring type designs are generally slender and more elongated in form. The spring type described herein may resemble or utilize any of these forms, but the shown design is more similar to a semi-elliptic, being attached to only one side of the joint (such as that shown in FIG. 3 for example, where a fulcrum resides on the non spring location to provide a pivot point and are generally padded for comfort or to improve function. The fulcrum shapes may vary to achieve these purposes). FIGS. 6A-6L are examples for differently shaped fulcrums, but additional three dimensional shapes or forms are anticipated depending on utility, comfort and location. In addition to various shapes, the fulcrums size may vary from smaller to larger diameters in order to vary the level of resistance, depending on the strength of the user, and/or their time proximity after a surgical procedure.

The spring members may be of a shape beyond a simple flat design that one might envision with a simple flat spring design; including, but not limited to other kinds of laminated leaf springs, other types of flat springs, semi-elliptical spring members, or curved. The exact shape is less important than the shape in combination with its function. However, the springs are generally no wider the width of the joint in question; primarily shown here as the knee joint. Thus the spring members are generally narrower than the width of the leg of the user. In this respect, a somewhat flat design works well. It should be clear that when the term "leaf spring" is used, it may include the various types of leaf and flat springs discussed even though not shown in the drawings herein.

The term "spring" is meant to include any resistive apparatus that provides resistance, passive or active, when a joint is extended; for example, when a knee is straightened, which is often medically described as "extended".

The described apparatus may also have alternatives that are made of other materials, but otherwise capable of providing similar rehabilitative resistance and benefits. Such spring like material may be fabricated of or with metal, alloys, or other materials, such as plastics of various types, fiberglass, Kevlar or other aramid fibers may be used, or other composites of a suitable material, or some combination of any of these materials capable of providing sufficient structural support for a brace device for any joint on a human body. Natural materials such as wood laminates or bamboo and bamboo laminates may be included as spring like elastic resistance materials utilized with the described brace embodiments.

The instant device provides resistance to a joint, extending the joint along its entire range (or a portion of that range) of motion. The instant device performs several functions, including, but not limited to a strengthening mode and a stretching mode. A strengthening mode for the knee joint occurs when the brace is installed on the back, rear, of the leg or the posterior portion of the leg or knee. These terms are all interchangeable and mean the same thing for the purposes of this disclosure; and, it provides resistance to straightening of the knee. The exercise is to start with a bent knee, and then the user actively straightens it. This movement with the resistance from the spring, exercises and strengthens the quadriceps muscle, primarily the vastus medialus oblique. These parts of the quadriceps muscle are weak due to inactivity during and after the surgery. This activity is important to restore strength so the leg can properly support the knee and body.

The stretching mode of the instant device occurs when the brace is installed on the front or anterior portion of the leg, along the side of the knee where the patella is located, and it passively pushes the knee straight in the extended position. The tightening device (could be a ratcheting device for example) allows a user to turn a knob or other control mechanism to shorten the strap attaching the spring to a leg, which in turn bends the spring over the fulcrum points above and below the knee, which results in a greater force exerted on stretching of the knee joint. This is a static stretch where the brace can be left on a user's leg for hours at a time. The purpose of this stretching is to break apart and/or prevent formation of post-operative scar tissue. If left intact, the scar tissue will reduce the range of motion of the knee which will interfere with normal walking or knee mobility and function.

The described devices may be utilized by a person of almost any size except perhaps small infants with underdeveloped joint function, which generally means a body weight just under to greater than 30 pounds. It may be possible to adapt the instant device to a lighter weight person, but the materials of the device would need to be very thin and flexible or otherwise adapted to smaller, weaker physiques and smaller functioning joints. Thus, any person of any weight, height, or size may utilize the instant devices adapted to fit them so long as they possess a sufficiently developed joint function. For this reason, the instant invention is configurable to support each of individuals in any size range. Basically, if a person is ambulatory and capable of walking, the device may be adapted to fit them and to be utilized by them. A person may be currently incapable of walking due to injury or being in a non-weight bearing orientation, but may still utilize the device in positions other than standing and walking in a weighted stance, such as laying supine or in a seated position. One may still bend the knee in the directions knees may bend and still utilize the device described herein without necessarily standing in a weight bearing position.

Disclosed herein is a device to provide a knee rehabilitation and exercise that allows a person to strengthen leg muscles after knee surgery. The device is shown to perform this function with the various designs described herein.

Another object of the invention is to provide a knee rehabilitation exercise device that helps increase the range of knee joint motion.

Another object of the invention is to provide a knee rehabilitation exercise device that can be easily used by a person without the need for assistance, or additional help from a caregiver.

A further object of the invention is to provide a knee rehabilitation exercise device that is lightweight, portable, and can be adjusted to fit a variety of leg lengths and diameters.

Yet another object of the invention is to provide a knee rehabilitation exercise device that can be fastened to a user's leg quickly and easily. It should be evident that devices designed to fit joints other than the knee (not shown) will also be adapted to fasten and unfasten quickly and easily as well. One method shown to perform this function is a ratcheting tension adjustment feature. Another method might be to utilize adjustable retention buckles or straps common to backpacking release straps and the like. The retention need only be accomplished in easy to use method for a user of the device. The strap (for example what is shown in FIG. 3, 304, may be flexible but inelastic; or, it may be flexible and also elastic, permitting some stretch to provide comfort and some self adjustment to its fit to the user's body.

Other objects and advantages of the present invention will become apparent from the following descriptions, taken in connection with the accompanying drawings; wherein, by way of illustration and example, an embodiment of the present invention is disclosed. Though not shown, it should be obvious that the device and designs described herein may also be applied to joints other than the knee. These joints include, but are not limited to the wrist, ankle, elbow, shoulder, hip, and even the spine and torso area. Additionally, there is no restriction to its possible veterinary applications with valued animals such as racing horses, or other breeding stock and the like.

The above and other objects, effects, features, and advantages of the present invention will become more apparent from the following description of the embodiments thereof taken in conjunction with the accompanying drawings.

BRIEF DESCRIPTION OF THE DRAWINGS

The accompanying drawings, incorporated in and forming a part of the specification, illustrate several arrangements of the present invention.

In the drawings.

DETAILED DESCRIPTION

Referring to FIGS. 1A through 7C, there is illustrated therein a new and improved knee or joint rehabilitative device. While "bungee" is used in some descriptions, it is not meant to limit the spring member to just one type of bungee when this term is used. The term describes an elastic spring member. There can be great variation in the type of elastic member used that can still function in the same manner. The spring members or elements may be of any kind of rope or cord which has elastic qualities which permits the spring member to stretch when extended or compress when extension is reversed or shortened. The spring members may be any type of elastic cords or may be made of a natural or synthetic rubber or other man made elastic material, or include the type of cords known as bungee or shock cords composed of one or more elastic strands forming a core and commonly covered in a sheath of woven material such as cotton, polypropylene, or other suitable material. Also, the spring member may include any other types of metal, coil, or composite springs or other type of cords that may function with the indicated embodiments or that may be configured for use described herein.

Additionally, when figures or descriptions describe attachment to a "leg", this term is meant to describe attachment to one or more points or places along the leg, regardless of whether the upper or lower leg are the locations of attachment. Medically, the term "upper leg" and "lower leg" together define the entire leg on either side of the knee joint (and ankle and foot). The use of "leg" is not meant to ignore these distinctions in any way.

Figure 1A:
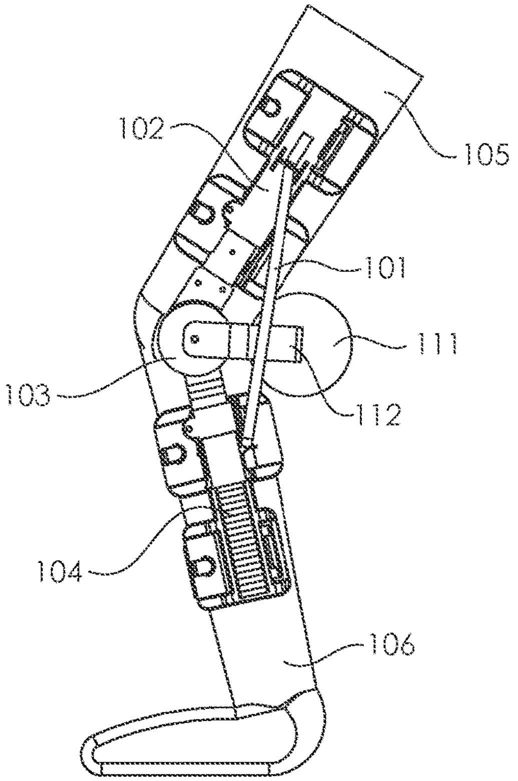
FIG. 1A is a side view of a knee brace with a resistance bungee.

FIG. 1A is a side view of a knee brace with a resistance bungee or other similar elastic type spring member, 101. The knee brace is comprised of the upper half, 102, the lower half, 104, the hinge, 103, and the rear knee support, 111. The upper half of the brace, 102, straps to the upper leg, 105, and the lower half of the brace, 104, straps to the lower leg, 106. The resistance bungee, 101, exerts a force pulling the upper brace half, 102, and the lower brace half, 104, together. The rear knee support, 111, straps onto the hinge, 103, with connector straps, 112, and provides support, which reassures the patient during the exercise. The purpose of this device is for the user to repeatedly straighten their leg, doing so overcomes the force from the bungee, 101. This exercise fires the quad muscles and helps them rebuild strength after knee surgery. Torsion springs could also be attached to the brace hinge, 103, to create a resistance torque around the knee.

Figure 1B:
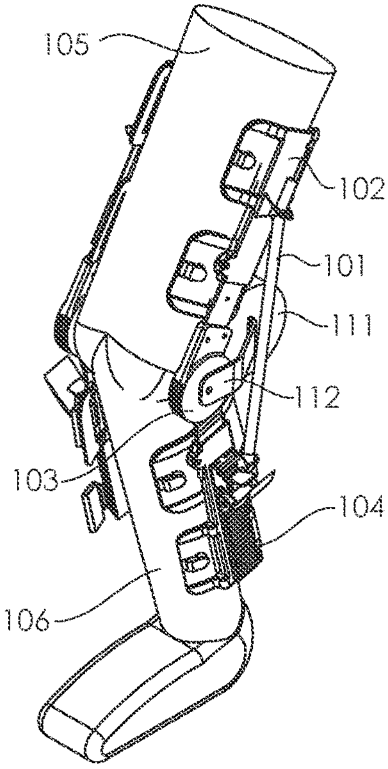
FIG. 1B is an isometric view of a knee brace with a resistance bungee.
Figure 1C:
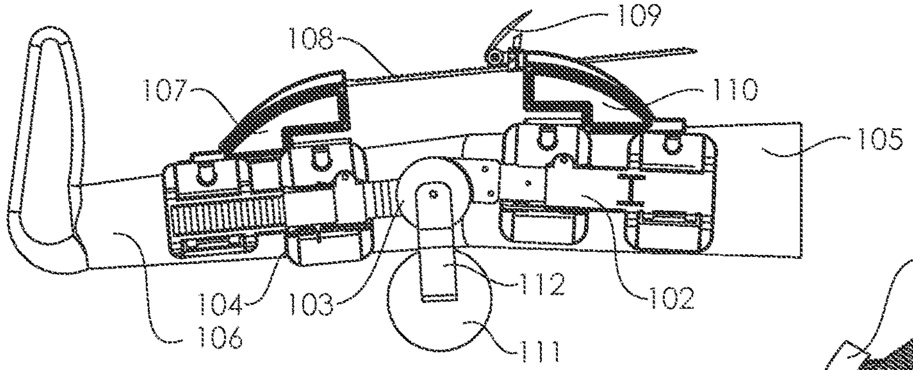
FIG. 1C is a side view of a knee brace with a ratcheting stretching device.
Figure 1D:
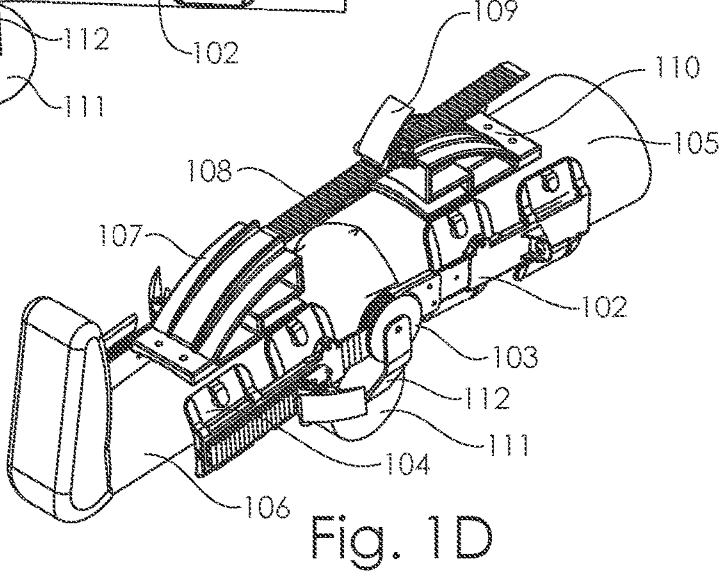
FIG. 1D is an isometric view of a knee brace with a ratcheting stretching device.

FIG. 1B is an isometric view of a knee brace with a bungee spring member, 101. FIG. 1C is a side view of a knee brace with a ratcheting stretching device. The stretching device is made up of a lower support, 107, an upper support, 110, a toothed strap, 108, and a ratchet buckle, 109. The lower support, 107, is fixed to the lower half of the knee brace, 104, and the upper support, 110, is fixed to the upper half of the knee brace, 102. This device is designed to pull the upper leg, 105, and the lower leg, 106, apart to straighten the leg. This is beneficial after knee surgery to help regain full range of motion. To straighten the leg, the user cranks the ratchet buckle, 109, which pulls the ratcheting strap, 108, through the buckle which brings the lower support, 107, closer to the upper support, 110. The ratchet buckle, 109, holds the stretch in place until it is released, so the stretch can be held for extended periods of time to break down scar tissue. The rear knee support, 111, can be used for the stretching, or it can be removed if that is preferred. One challenge with this embodiment was that it was found that the stretching forces were not consistently applied perpendicular to the leg. Therefore, instead of pulling the leg straight as desired, the prototype for this embodiment tended to pull the brace together, which in turn increased the likelihood of slippage along the leg. In response, a user would have to hold the top of the brace with one hand while tightening with the other to keep the device fixed at the desired location. FIG. 1D is an isometric view of a knee brace with a ratcheting stretching device.

Figure 2A:
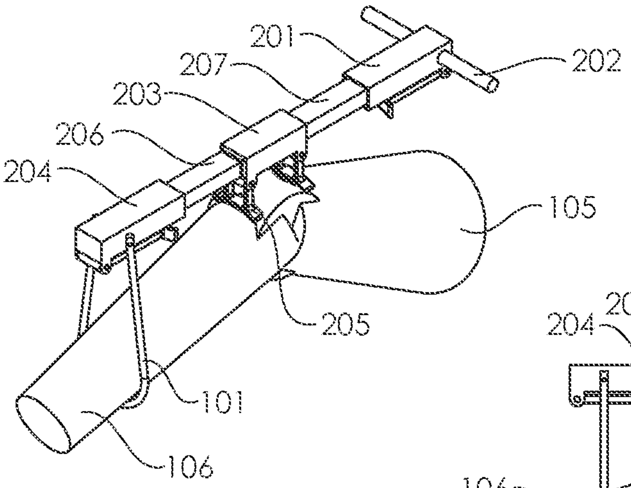
FIG. 2A is an isometric view of a post and beam leg stretching device attached to a leg.

FIG. 2A is an isometric view of a post and beam leg stretching device attached to a leg. The device is made up of an upper slider, 201, a mid section, 203, and a lower slider, 204.

The mid section, 203, has an extending lower rail, 206, and an extending upper rail, 207, which the sliders adjust on. The upper slider has extending handle grips, 202, for the user to hold. When the device is in the stretching mode, the middle legs, 205, fold open, so the device is supported just above and below the knee. A bungee cord, 101, is wrapped around the user's lower leg, 106. To stretch the leg, the user can push down on the upper slider handle grips, 202.

Figure 2B:
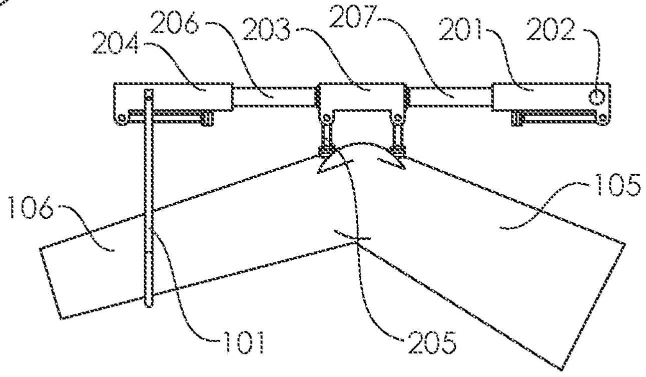
FIG. 2B is a side view of a post and beam leg stretching device attached to a leg.
Figure 2C:
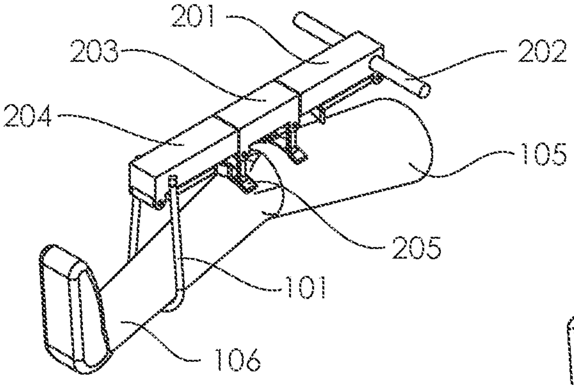
FIG. 2C is an isometric view of a post and beam leg stretching device attached to a smaller leg.
Figure 2D:
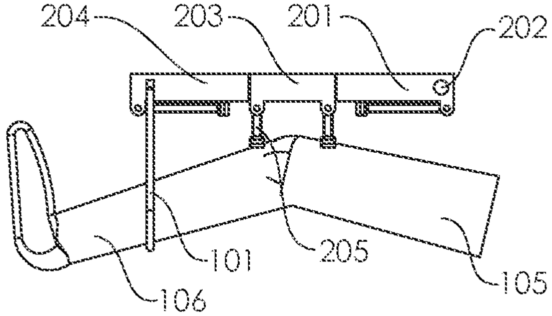
FIG. 2D is a side view of a post and beam leg stretching device attached to a smaller leg.

FIG. 2B is a side view of a post and beam leg stretching device attached to a leg. FIG. 2C is an isometric view of a post and beam leg stretching device attached to a smaller leg. For the smaller user, the lower slider, 204, and upper slider, 201, are adjusted in towards the mid section 203. FIG. 2D is a side view of a post and beam leg stretching device attached to a smaller leg.

Figure 2E:
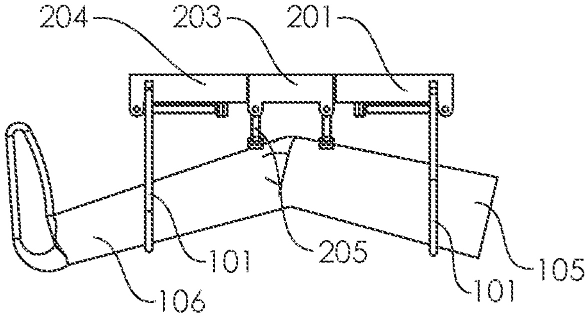
FIG. 2E is a side view of a post and beam leg strengthening device attached to a smaller leg, with elastic spring members.
Figure 2F:
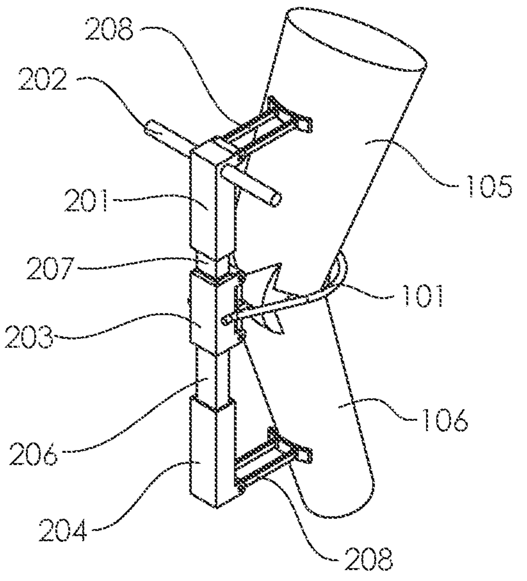
FIG. 2F is an isometric view of a post and beam leg strengthening device attached to a lager leg, with an elastic spring member.
Figure 2G:
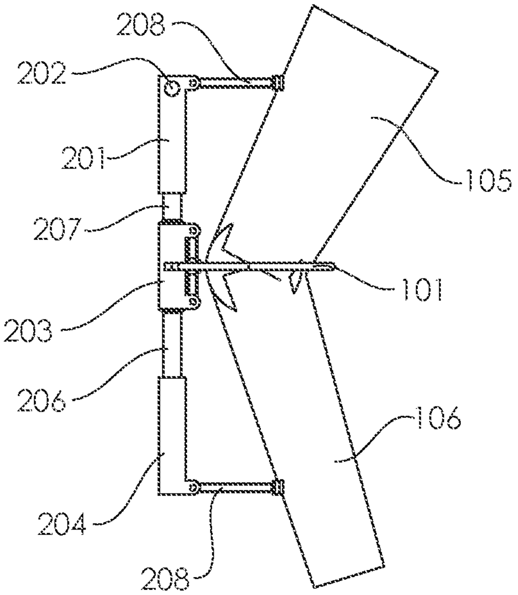
FIG. 2G is a side view of a post and beam leg strengthening device attached to a larger leg.
Figure 2H:
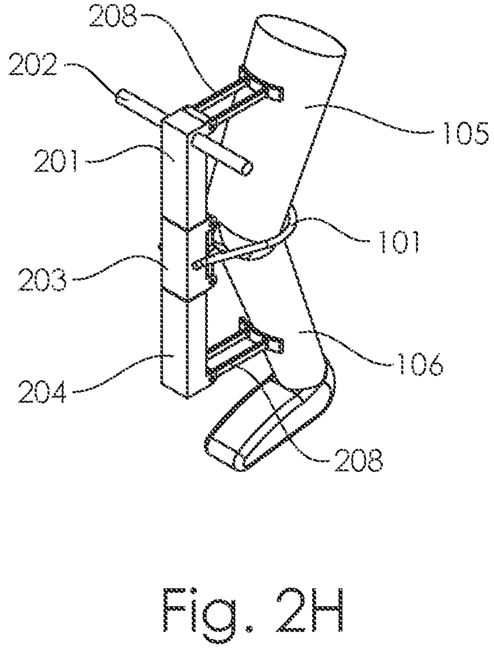
FIG. 2H is an isometric view of a post and beam strengthening device attached to a smaller leg.
Figure 2I:
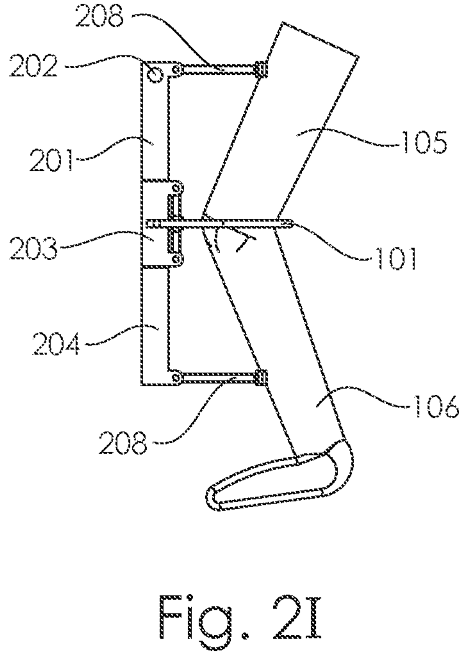
FIG. 2I is a side view of a post and beam strengthening device attached to a smaller leg.

FIG. 2E is an isometric view of a post and beam leg strengthening device attached to a large leg. For this exercise, the bungee cord, 101, wraps around the back of the knee and attaches to the brace mid section, 203. The outside legs, 208, are extended so the device is supported at the top and bottom of the leg. To perform the exercise, the user straightens their knee, which stretches the bungee, 101, thereby creating resistance. This exercise is usually performed standing, so the user can hold the upper slider hand grips, 202, to support the brace. FIG. 2F is a side view of a post and beam leg strengthening device attached to a larger leg. FIG. 2G is an isometric view of a post and beam strengthening device attached to a small leg. To adjust for the small leg, the lower slider, 204, and upper slider, 201, are adjusted in towards the mid section, 203. FIG. 2H is a side view of a post and beam strengthening device attached to a small leg.

Figure 3A:
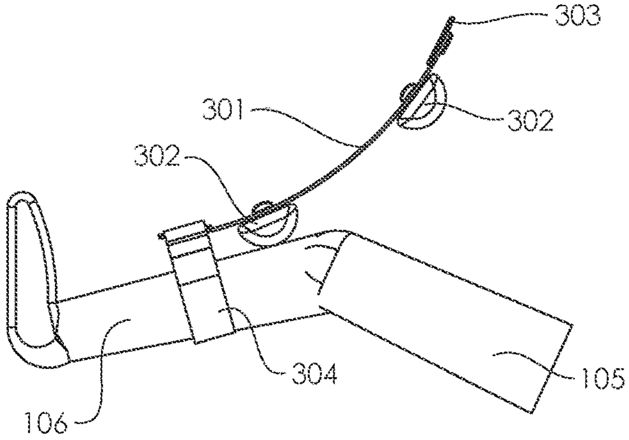
FIG. 3A is a side view of a leaf spring knee brace.

FIG. 3A is a side view of a leaf or flat spring knee brace. It is a preferred embodiment or design in that it is more compact and less likely to pivot in an undesirable manner. The leaf spring, 301, is a flat, flexible sheet of material that can be bent when loaded. In this configuration, the brace is partially installed for the stretching exercise. The lower brace strap, 304, is wrapped around the user's lower leg, 106. The position of the brace fulcrums, 302, (which can be padded for comfort), can be adjusted above and below the surgical incision sites per the user's tolerance and provide a pivot point for the leaf spring, 301, on the front of the leg. The closer to the knee joint the fulcrums, 302, are placed, the greater the force the leaf spring will be able to produce to passively push or move the knee into extension. Thus, it is preferable to place the upper fulcrum, 302, just proximal to the top of the patella and the lower fulcrum, 302, just distal to the tibial tuberosity and/or surgical incision site. The brace plate, 303, is extending up in a free state and is ready to be tightened. The spring can be made flexible enough to permit a range of motion up to and including a full range of motion for the knee joint.

Figure 3B:
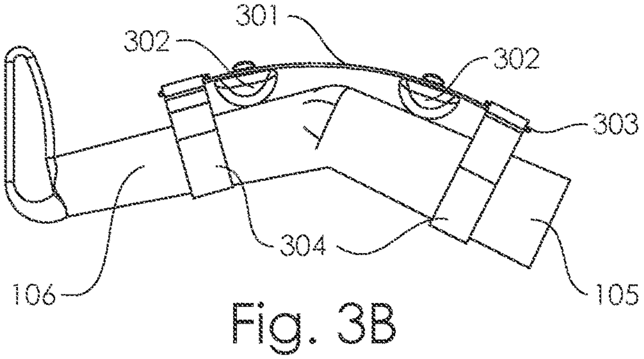
FIG. 3B is a side view of a leaf spring knee brace in the stretching configuration.

FIG. 3B is a side view of a leaf spring knee brace in the stretching configuration. When the leg is stretched, the tendons elongate, scar tissue is broken down, and the muscles of the hamstrings and gastrocnemius are stretched. This shows how it looks after the user also straps down the top plate, 303, to the upper leg, 105. The bent leaf spring, 301, pivots on the fulcrums, 302, and exerts force on the upper and lower leg, pushing the knee into passive extension. The brace straps, 304, can be tightened or loosened to adjust the stretching force from spring, 301. The brace provides a static stretch, which is meant to be applied for long periods of time. The stretching forces can minimize and/or gradually break down scar tissue which formed after the surgery. The scar tissue prevents the knee joint from achieving its full range of motion, and it is critical to spend enough time stretching to get the full passive knee extension range of motion back.

Figure 3C:
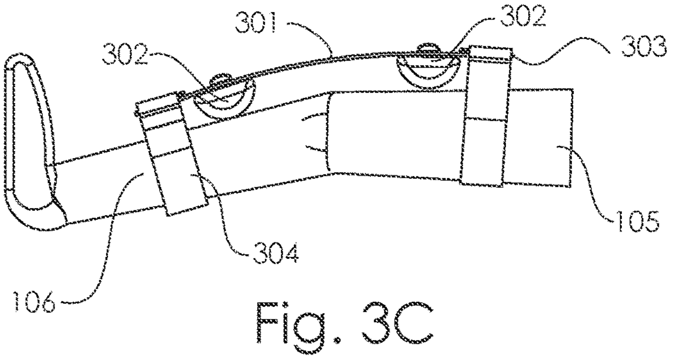
FIG. 3C is a side view of a leaf spring knee brace that has begun stretching a knee.

FIG. 3C is a side view of a leaf spring knee brace that has started to stretch the user's knee. The spring has pulled the user's knee straighter than it was in FIG. 3B.

Figure 3D:
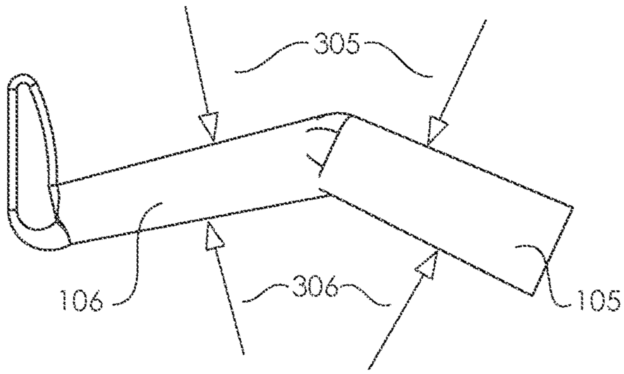
FIG. 3D shows the forces exerted on the leg when it is being stretched by the leaf spring.

The spring and leg equalize and result in the beneficial stretch for the user to regain range of motion. FIG. 3D shows the forces exerted on the leg when it is being stretched by the leaf spring, 301. 305 are the two reaction forces on the leg from the fulcrums, 302. 306 are the two forces transferring through the two brace straps, 304, from the ends of the leaf spring, 301. This device is adjustable to fit a wide range of users. The location of the fulcrum pads, 302, may be moved to any place along user's upper or lower leg, 105 and 106; or along the spring member, 301. Additionally, the retention devices (in this case, straps, 304), both above and below the knee may be moved to better fit the user's needs and dimensions, either up or down the portion of a user's leg above and below the knee. Because these members can be moved in extremely tiny increments, the adjustability is essentially infinite between the two retention devices, 304. Additionally, the size, shape, and diameter of the fulcrums may be either enlarged or reduced in order to increase or decrease the resistance the user experiences, whether active or passive; and, whether the spring member is along the front of the knee cap and user's leg, FIGS. 3B and 3C; or behind the user's knee joint along the rear of the leg, FIGS. 3E and 3F.

Figure 3E:
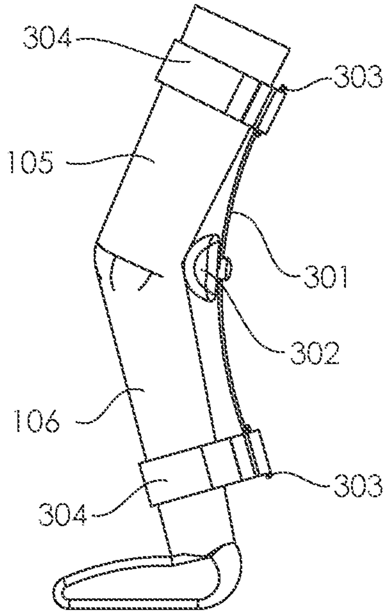
FIG. 3E is a side view of a leaf spring knee brace in the strengthening configuration.

FIG. 3E is a side view of a leaf spring knee brace in a strengthening configuration. To switch from the stretching configuration to the strengthening configuration, the brace is rotated around the leg and installed behind the knee. In this configuration, only one support fulcrum, 302, is used as a pivot point located behind the back of the knee in the general area of the popliteal fossa. Fulcrums, 302, of various diameters can be used in this configuration. The greater the diameter of the fulcrum, 302, the greater the resistance the spring will be able to provide. Thus, a smaller diameter fulcrum, 302, can be used during the early stages of the knee rehabilitation and progressed to a larger diameter fulcrum, 302, as the user's quadriceps strength increases.

This shows the leaf spring, 301, at rest. The advantages of this design are even more evident in that the same spring, 301, and strap, 304, are able to be utilized both in front of the knee, and behind the knee, eliminating the need for additional devices. This is a great advantage for reducing weight, complexity, and the need for multiple devices. The instant device performs multiple functions when moved to the front of the knee and leg or to the rear of the knee and leg; and by altering the size, location, and shape of the fulcrums.

Although not shown, it has been conceived that any of the fulcrums may be designed to enlarge or reduce in diameter individually by changing its own size. For example, a fulcrum could incorporate one or more bladders that may be filled with a fluid or solid material that is adjustable in volume, which then increases or decreases the size of said fulcrum. Or, one fulcrum may be configured to add or remove layers of matching or mixed material (like foam, pellet or fluid filled bladder) which fits or couples to the fulcrum to enlarge it when needed or desired; and to reduce when needed or desired.

Figure 3F:
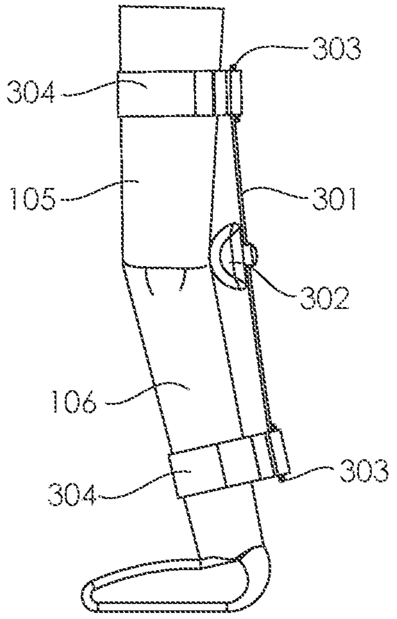
FIG. 3F is a side view of a leaf spring knee brace in the strengthening configuration when the leaf spring is deformed.
Figure 3G:
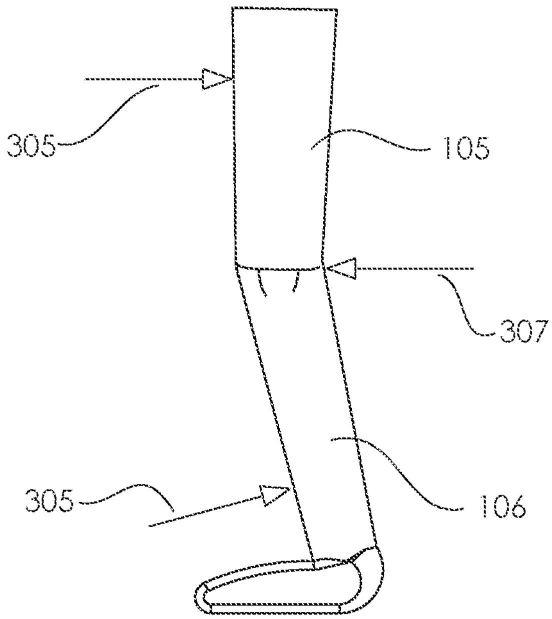
FIG. 3G is a side view showing the forces acting on the leg, resisting its straightening motion.

FIG. 3F is a side view of a leaf spring knee brace in the strengthening configuration when the leaf spring, 301, is deformed. This is the second position of the exercise when the user straightens their knee which straightens the curved leaf spring, 301, flat. Straightening the leaf spring, 301, requires force from the quadriceps muscles which helps rebuild their strength after surgery. When the user straightens his or her knee as shown in FIG. 3F, the leaf spring is straightened and thereby puts a resistive force on the user's quadriceps muscles that are associated with the knee joint, specifically the rectus femoris, vastuslateralis, intermedialis and vastusmedialus oblique muscles. By repeatedly firing the quadricep muscles, the user can help increase the strength of the muscles associated with the knee joint after knee surgery. To "fire" a muscle refers to the electrochemical process of generating tension within a muscle during contraction. The present invention can also be used as a leg strengthening exercise for non-surgical conditions to keep the muscles around the knee in top shape. The exercise can be done by an individual without the help of an assistant. FIG. 3G is a side view showing the forces acting on the leg, resisting its straightening motion. 307 demonstrates the direction of the force provided by the fulcrum, 302, which is placed between the back of the knee and the leaf spring, 301. 305 demonstrates the direction of the forces provided by the two brace straps, 304.

Figure 4A:
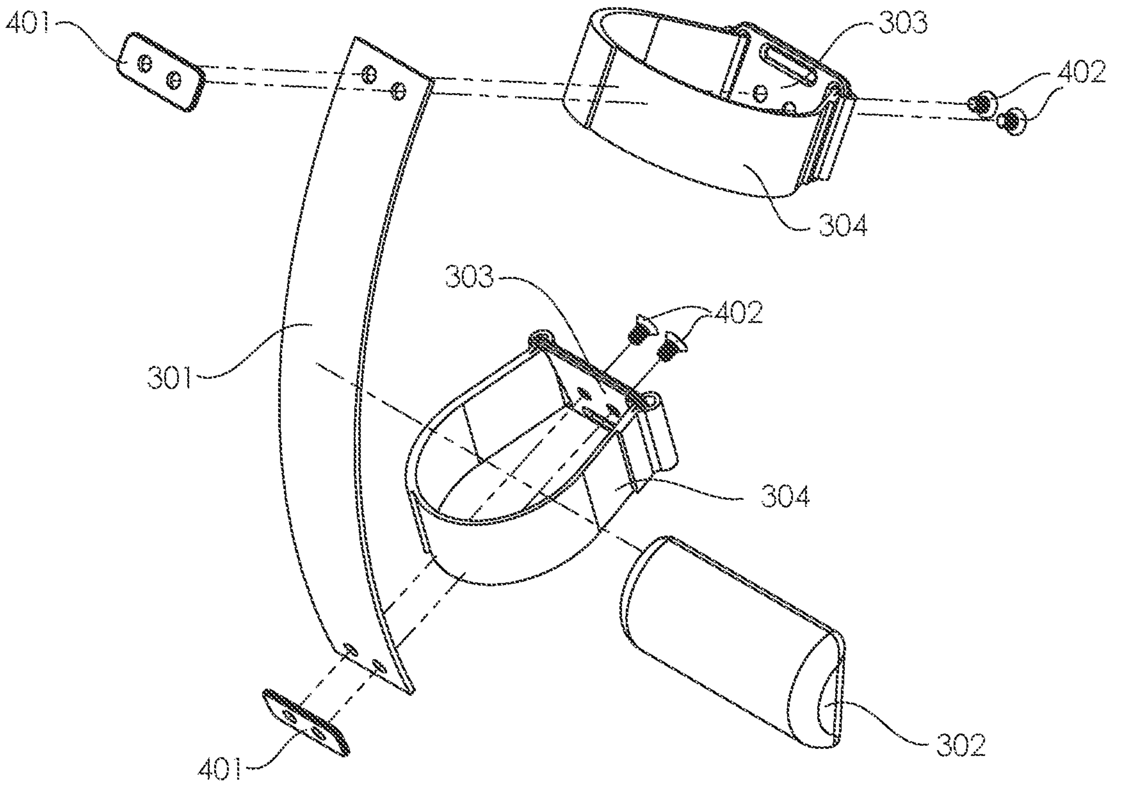
FIG. 4A is an exploded view of the leaf spring knee brace.
Figure 4B:
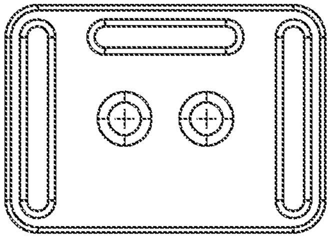
FIG. 4B is a front view of a leaf spring knee brace plate.
Figure 4C:
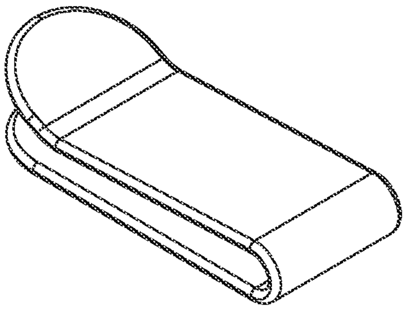
FIG. 4C is an isometric view of a padded fulcrum spring clip.

Other configurations not shown in the drawings are also conceived. For example, a tensioning strap may also be positioned from the center of 301, FIG. 3A to a fulcrum positioned behind the knee as that shown in 111, FIG. 1C. In an additional configuration, one could combine the device shown in FIG. 3C with FIGS. 1A-1D to enhance lateral knee support shown in 3C, and the flex performance shown FIG. 1C. One could combine the two devices shown in FIG. 3C and FIG. 1C FIG. 4A is an exploded view of the leaf spring knee brace. It is made up of the leaf spring, 301, the brace plates, 303, the brace straps, 304, the support fulcrums, 302, nut plates, 401, and four screws, 402. FIG. 4B is a front view of a leaf spring knee brace plate. It has counter sunk holes for the mounting screws. There are 3 slots for straps cut out. The two on the side are for the brace straps, 304, and the one on the top is for an optional vertical strap which the user can hold onto to ensure the brace does not slip down the leg. The brace strap, 304, is permanently sewn to one slot, and it runs through the other slot and Velcro's to itself once it is tight. FIG. 4C is an isometric view of a fulcrum spring clip. These clips are attached to the back of the fulcrums, 302, and they clip onto the leaf spring, 301. These allow the users to quickly add, remove, and reposition the fulcrums.

Figure 5A:
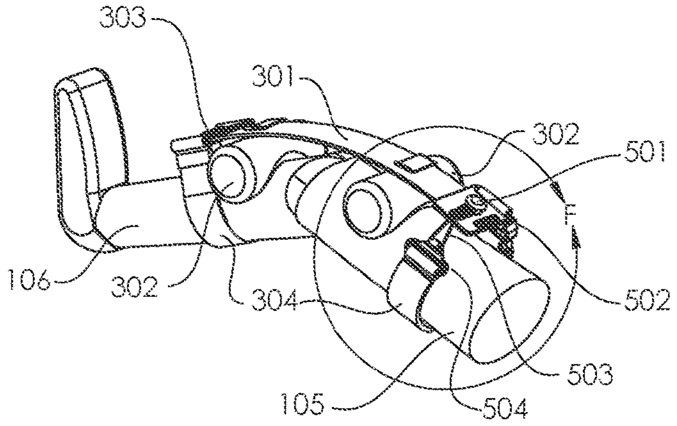
FIG. 5A is an isometric view of a leaf spring knee brace with a ratcheting tension adjustment feature.
Figure 5B:
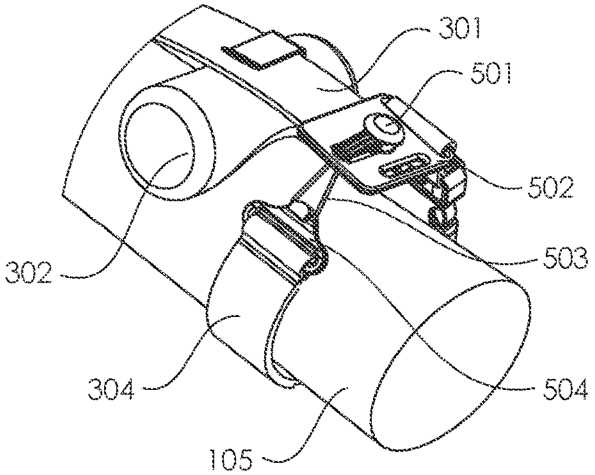
FIG. 5B is a detailed isometric view of the top of the leaf spring knee brace with a ratcheting tension adjustment feature.

FIG. 5A is an isometric view of a leaf spring knee brace that has a ratcheting tension adjustment feature or device. This brace allows the user to put the brace on loose, and then dial in the perfect amount of tension for the stretching exercise. This is helpful, because it is difficult to set the strap to the right position especially because it is easy to apply a painful amount of force to a weak knee. FIG. 5B is a detailed isometric view of the top of the ratcheting leaf spring knee brace. This configuration requires a different top plate, 502, that has the mounting for the ratchet. The top strap, 304, has a hook buckle, 504 attached to one end. This hook buckle, 504, hooks onto the retractable wire, 503. The hook buckle, 504, could also be permanently attached to the retractable wire, 503. The retractable wire, 503, can be drawn in or released by turning the ratcheting knob, 501.

Figure 5C:
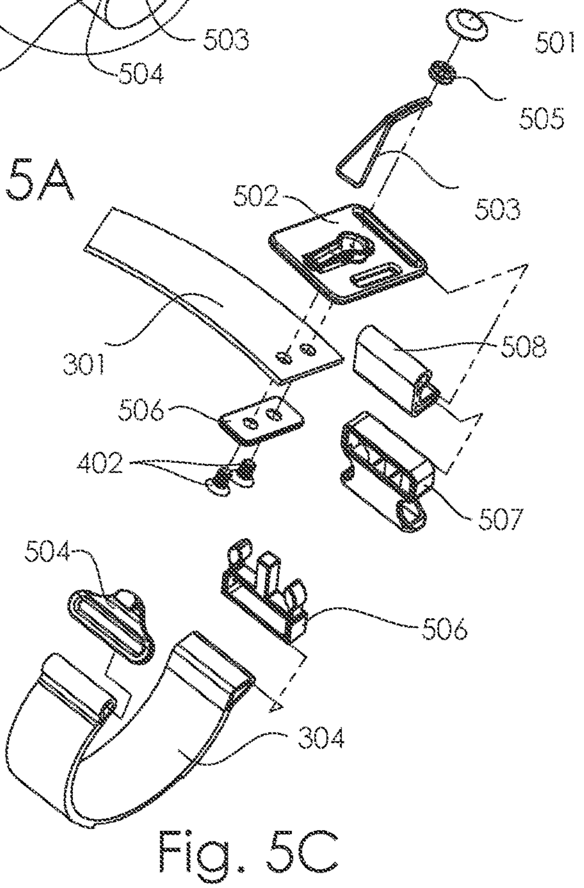
FIG. 5C is an exploded isometric view of the leaf spring knee brace with a ratcheting tension adjustment feature.
Figure 5D:
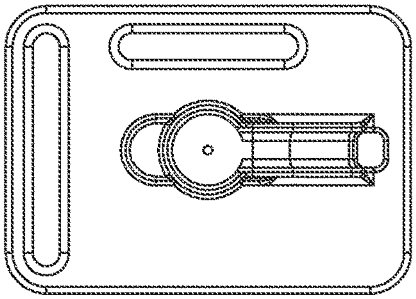
FIG. 5D is a front view of the ratcheting top plate.
Figure 5E:
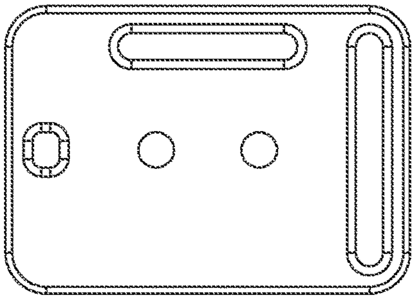
FIG. 5E is a rear view of the ratcheting top plate.

FIG. 5C shows an exploded isometric view of the ratcheting leaf spring knee brace. In this configuration, the screws, 402, go through the washer plate, 506, the leaf spring, 301, and they thread into the tapped holes on the back of the ratcheting top plate, 502. There is a wire spool, 505, that has the ratchet notches on the top, and winds in the retractable wire, 503. The end of the top strap, 304, has a male buckle clip, 506, looped onto it. The length of the strap can be adjusted with the male buckle clip, 506. The female buckle clip, 507, is sewn onto a short strap, 508, which is sewn onto the top plate, 502. This system allows the user to quickly adjust the strap, 304, to the approximate desired length and snap the buckles, 506 and 507, together easily. Then they can dial in more stretch by turning the ratcheting knob, 501.

Figure 6A:
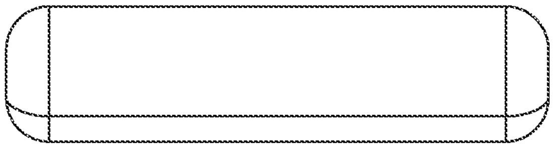
FIG. 6A is a front view of a half circle fulcrum.
Figure 6B:
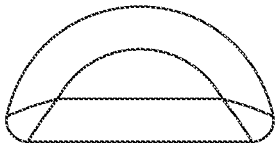
FIG. 6B is a side view of a half circle fulcrum.
Figure 6C:
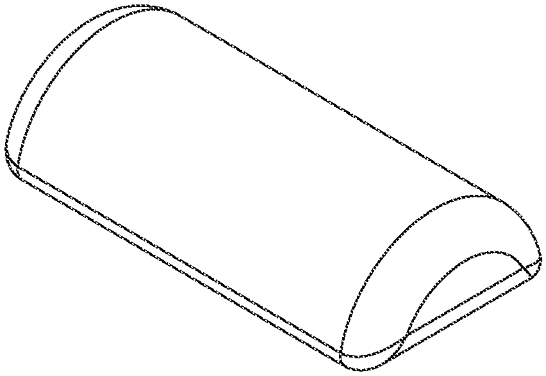
FIG. 6C is an isometric view of a half circle fulcrum.
Figure 6D:
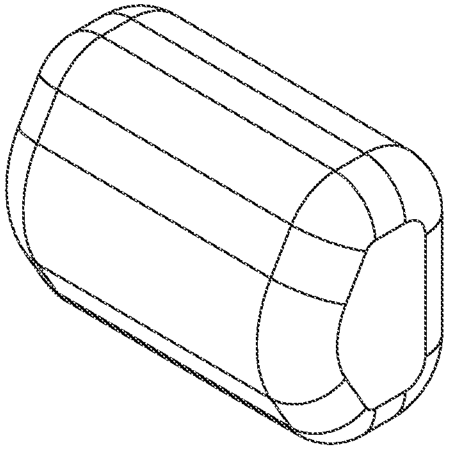
FIG. 6D is an isometric view of an angled fulcrum.
Figure 6E:
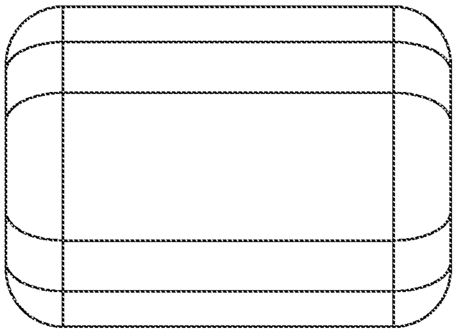
FIG. 6E is a top view of an angled fulcrum.
Figure 6F:
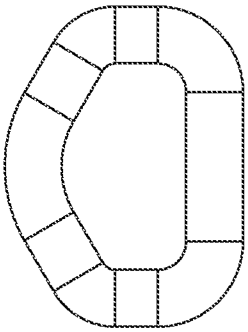
FIG. 6F is a side view of an angled fulcrum.
Figure 6G:
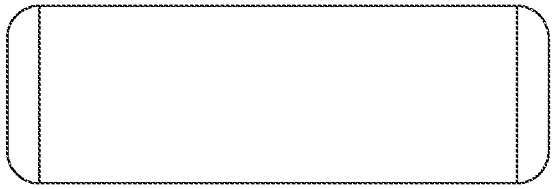
FIG. 6G is a front view of a full round fulcrum.
Figure 6H:
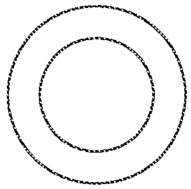
FIG. 6H is a side view of a full round fulcrum.
Figure 6I:
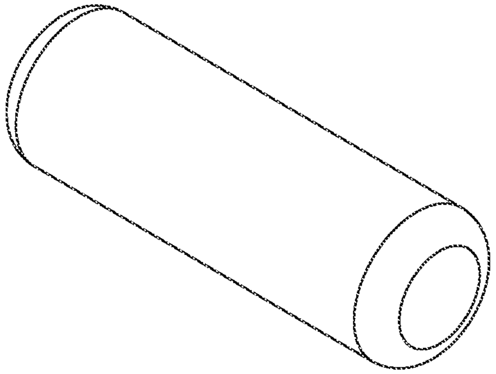
FIG. 6I is an isometric view of a full round fulcrum.
Figure 6J:
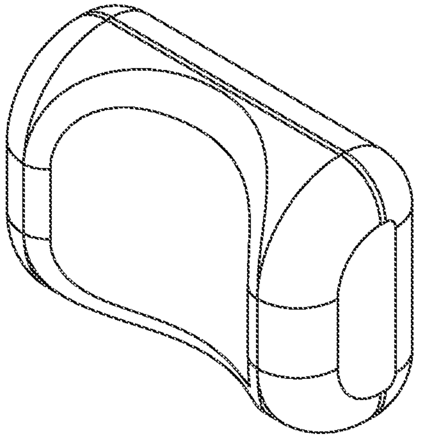
FIG. 6J is an isometric view of a shaped leg fulcrum.
Figure 6K:
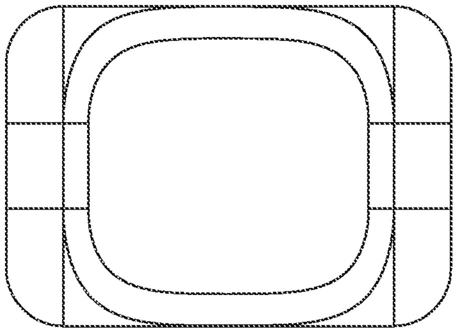
FIG. 6K is a top view of a shaped leg fulcrum.
Figure 6L:
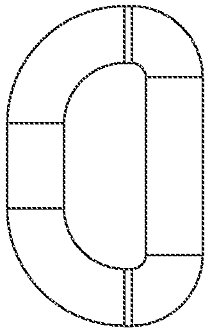
FIG. 6L is a side view of a shaped leg fulcrum.
Figure 7A:
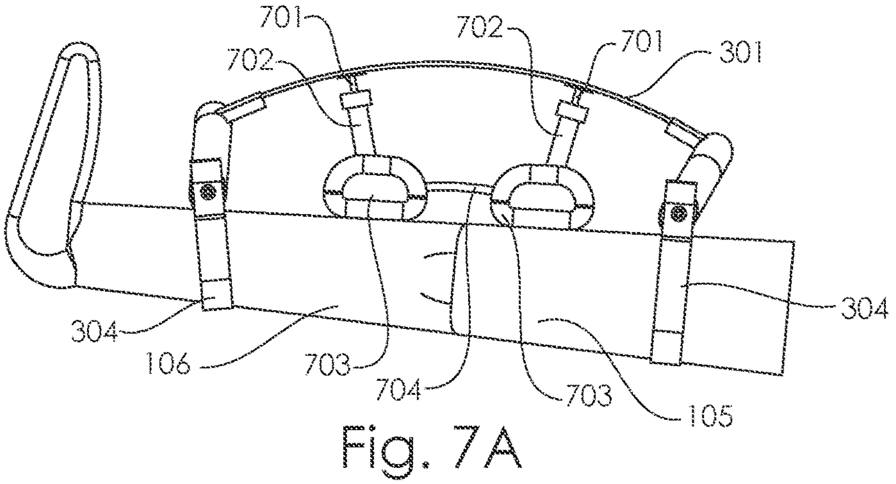
FIG. 7A shows a leaf spring leg brace with auto adjusting fulcrums.
Figure 7B:
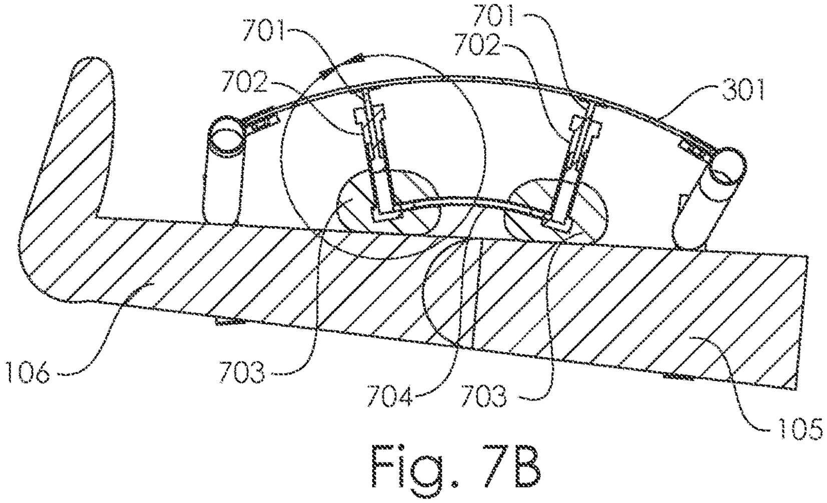
FIG. 7B is a cross section view of a leaf spring leg brace with auto adjusting fulcrums.
Figure 7C:
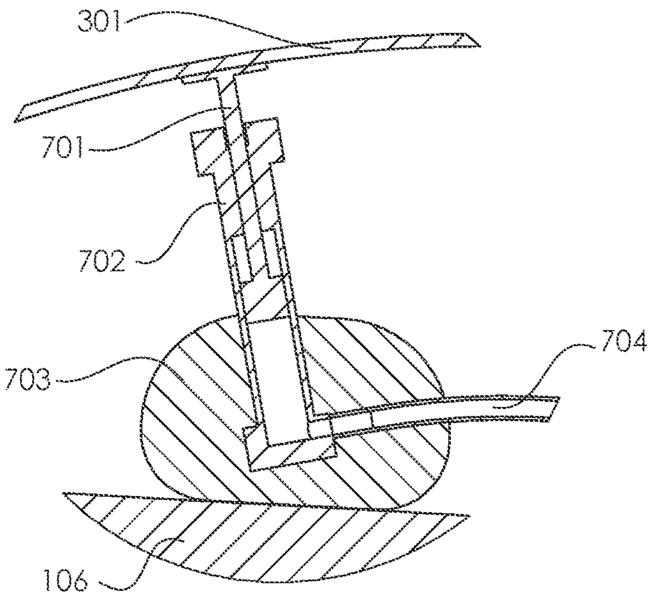
FIG. 7C is a cross section detail view of a leaf spring leg brace with auto adjusting fulcrums.

FIGS. 6A-6L show various "fulcrums" in the form of pads or cushioning or resilient devices that provide a pivot point between the leaf spring and the user's leg. Such fulcrums generally separate the spring member from substantially contacting the knee joint. "Generally" is defined for the purpose of this disclosure such that contact may occur during use, but it is lessoned via the use of these fulcrums. Also, these fulcrums provide a pivot point for the user during movement or non movement of the joint. For example, a fulcrum, 302, helps keep a spring member, 301, from continuous contact with a user's knee joint. The fulcrum may be made of various materials, including but not limited to, foams of different densities and rigidities; air bladders, liquid bladders, plastics, or the like of different densities and rigidities. FIG. 6A shows a front view of a half circle fulcrum. This is a versatile fulcrum shape that can be used anywhere along the leg. FIG. 6B is a side view of a half circle fulcrum. FIG. 6C is an isometric view of a half circle fulcrum. FIG. 6D is an isometric view of an angled fulcrum. This fulcrum is meant to fit behind the knee and provide full support. FIG. 6E is a top view of an angled fulcrum. FIG. 6F is a side view of an angled fulcrum. FIG. 6G is a front view of a full round fulcrum. This fulcrum provides a nice soft surface where it contacts, but it is slightly harder to mount because there is no flat side. FIG. 6H is a side view of a full round fulcrum. FIG. 6I is an isometric view of a full round fulcrum. FIG. 6J is an isometric view of a shaped leg fulcrum. This fulcrum is specially shaped to fit anatomically against or adjacent to the curve of the user's leg. This provides comfort when used both on the front of the leg, and behind the knee. FIG. 6K is a top view of a shaped leg fulcrum. FIG. 6L is a side view of a shaped leg fulcrum. FIG. 7A shows a leaf spring leg brace with auto adjusting fulcrums. This device has hydraulic cylinders, 702, in between the leaf spring, 301, and the brace fulcrums, 703. When the piston, 701, of one cylinder, 702, is depressed, the fluid transfers through the tube, 704, which extends the other piston. When both of the pistons are attached to the leaf spring, 301, it behaves as a self balancing system. If one side of the brace is too loose, the piston will extend until it is equally loaded to the other piston. FIG. 7B is a cross section view of a leaf spring leg brace with auto adjusting fulcrums. FIG. 7C is a cross section detail view of a leaf spring leg brace with auto adjusting fulcrums. This shows how the piston, 701, is attached to the leaf spring, 301, and the cylinder body, 702, is fixed inside the fulcrum, 703.

Figure 8A:
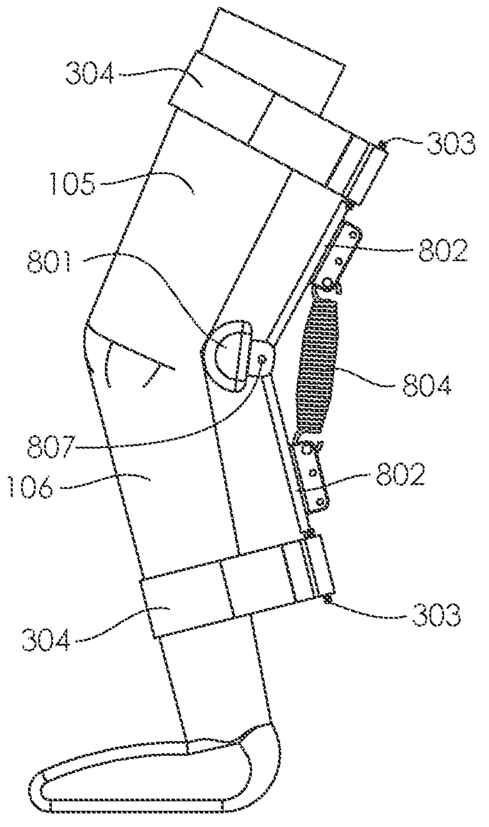
FIG. 8A shows an extension spring brace system configured for strengthening.

FIG. 8A shows an extension spring brace system configured for strengthening. This is an alternate to the leaf spring design, where instead of bending the leaf spring; resistance is created by a spring loaded linkage. This brace can also be used on the front of the leg to stretch the leg by adding two leg fulcrums, just like the leaf spring design. The linkage is comprised of two rigid bars, 802, that are connected with a pivot pin, 807. An extension spring, 804, attaches to the two bars, 802, and it exerts a force as it is stretched. Any other type of spring could be used as well such as torsion springs, air springs, and elastic bands.

Figure 8B:
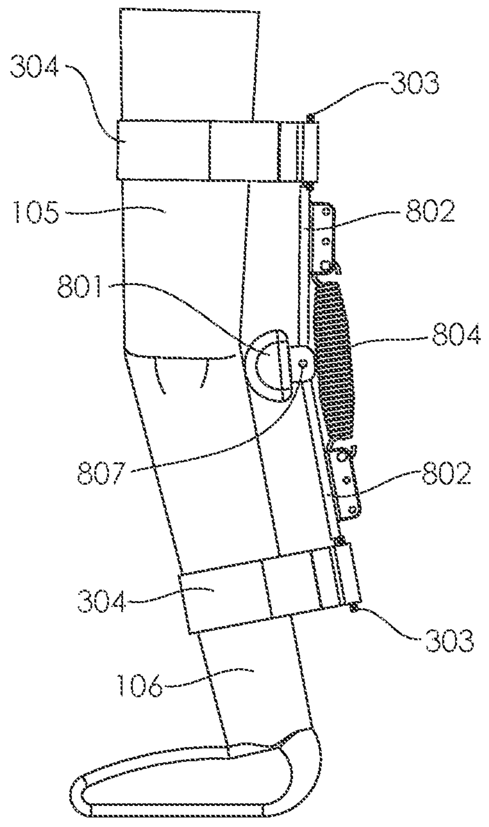
FIG. 8B shows the extension spring brace system configured for strengthening when the leg is straightened.
Figure 8C:
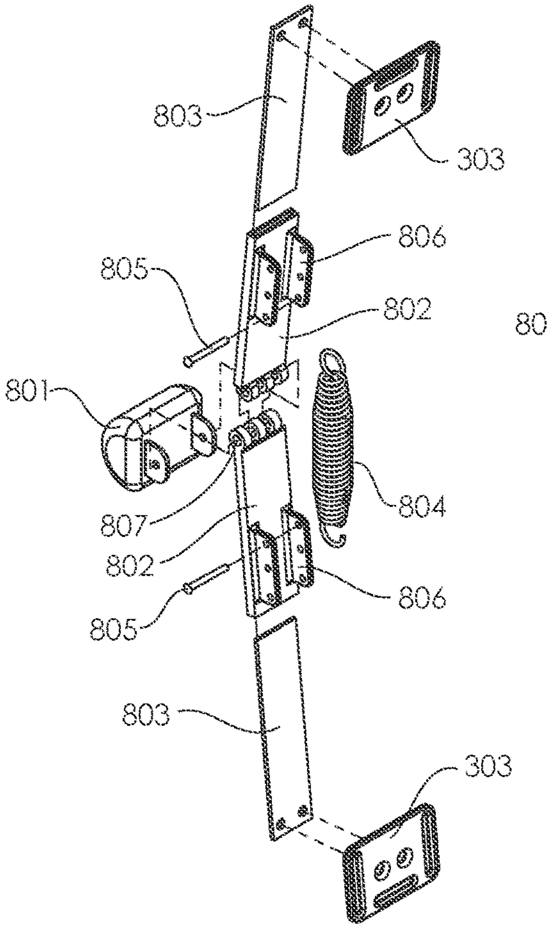
FIG. 8C is an exploded view of the extension spring brace system.

FIG. 8B shows the extension spring brace system configured for strengthening when the leg is straightened. This forces the rigid bars, 802, to straighten and that causes the spring, 804, to elongate. The spring, 804, creates resistance which strengthens the quadricep muscles. FIG. 8C is an exploded view of the extension spring brace system. It has a fulcrum, 801, in front of the pivot point, 807, which presses on the back of the knee. The rigid bars, 802, have internal bars, 803, which slid in and out can be adjusted for different size legs. The top plate, 303, bolts onto the internal bars, 803. There are pin brackets, 806, on each rigid bar, 802, which have multiple holes for the spring pin, 805, for adjusting to different preloads. The spring, 804, hooks onto the two spring pins, 805. FIG. 8D is an isometric view of the extension spring brace system configured for strengthening, set to the softest spring preload.

Figure 8E:
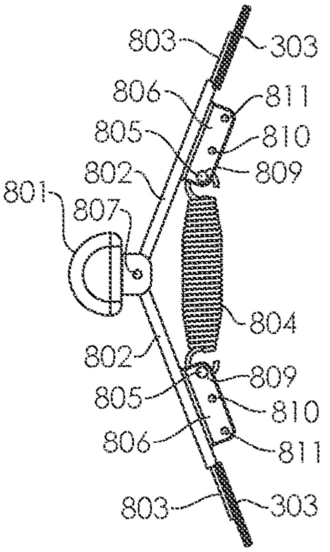
FIG. 8E is a side view of an extension spring brace system configured for strengthening, in the relaxed position, set to the softest spring preload.
Figure 8F:
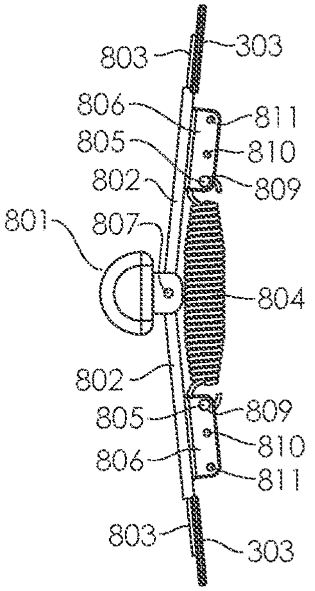
FIG. 8F is a side view of the extension spring brace system.
Figure 8D:
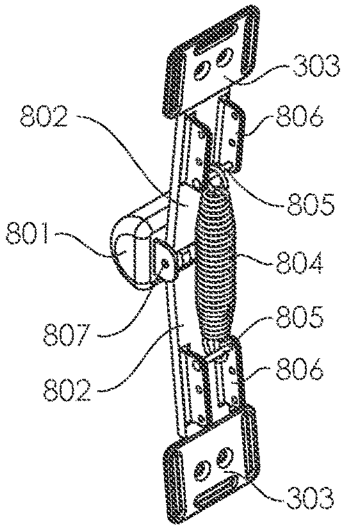
FIG. 8D is an oblique view of the extension spring brace system.

FIG. 8E is a side view of an extension spring brace system configured for strengthening, in the relaxed position, set to the softest spring preload. This embodiment shows 3 different pin holes, 809, 810, 811, but there can be any number. The pin, 805, is installed in the closest hole, 809. This means that the spring does not have much stretch when it is installed on a bent leg. FIG. 8F is a side view of an extension spring brace system configured for strengthening, in the stretched position, set to the softest preload. This shows that when the rigid bars, 802, are straightened, the spring, 804, is stretched. Since the spring, 804, is attached to the closest holes, 809, it doesn't end up with a lot of stretch when the rigid bars, 802, are straightened.

Figure 8G:
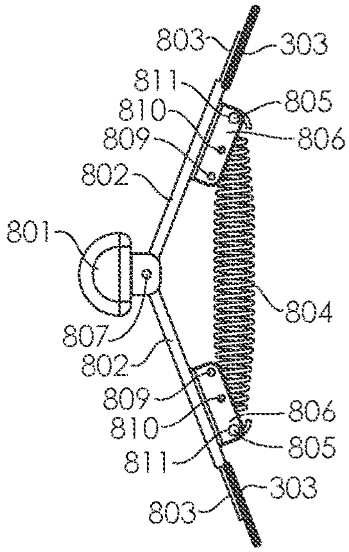
FIG. 8G is a side view of an extension spring brace system configured for strengthening.

FIG. 8G is a side view of an extension spring brace system configured for strengthening, in the relaxed position, set to the highest preload. In this view, the spring pin, 805, is moved to the farthest holes, 811. This shows that the spring, 804, is already stretched significantly when it is in the relaxed position.

Figure 8H:
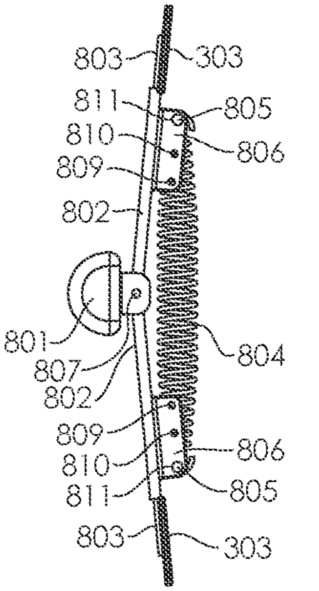
FIG. 8H is a side view of an extension spring brace system configured for strengthening.

FIG. 8H is a side view of an extension spring brace system configured for strengthening, in the stretched position, set to the highest preload. This shows that by setting the spring to the highest preload, it results in a much higher stretch when the rigid bars, 802, are straightened. This results in a higher resistance and better workout that users can work up to.

Other configurations, although not shown in the drawings are included. FIGS. 8A-H can be used in a similar manner as FIGS. 3A-C by reconfiguring 801 so that is interfaces with the leg just above and below the knee in a similar position to that of 205 in FIGS. 2A-I. The device shown in FIGS. 8A-H could also be configured with a spring that is parallel or in line with the hinge. Additionally, FIGS. 8A-H could also have two hinges where they are positioned equally distant from the center to approximate the forces placed on the knee in a manner similar to that shown in FIGS. 3A-C.

It should be apparent that the spring shown, 804, may also be another type of spring member such as an elastic spring member akin to a bungee; or a modified leaf type spring with various levels adjustment for length and resistance levels as options. Additionally, such spring members may be adjustable in themselves, or replaceable, to tailor the resistance force of the spring member.

While the invention has been described in connection with preferred embodiments, it is not intended to limit the scope of the invention to the particular forms set forth, but on the contrary, it is intended to cover such alternatives, modifications, and equivalents as may be within the spirit and scope of the invention as described and claimed herein.

We claim:

1. A joint rehabilitation device comprising:

a hinged brace configured to be secured to a leg and having upper and lower brace portions coupled by a pivot;

adjustable straps configured to secure the joint rehabilitation device onto both an upper leg and a lower leg of a user;

a flat leaf spring configured to be oriented along a front of a user's knee joint and connected to the upper and lower brace portions by brace plates, nut plates, and screws; and at least one support forming a fulcrum oriented adjacent to the pivot and including a resilient pad and a fulcrum spring clip attached to a back of the resilient pad, the fulcrum spring clip releasably coupled to the flat leaf spring and configured to permit the resilient pad to be repositioned along the flat leaf spring, wherein the resilient pad is configured to separate the flat leaf spring from the user's knee joint and prevent the flat leaf spring from contacting the user's knee joint during a partial range of motion.

2. The joint rehabilitation device of claim 1, wherein the flat leaf spring is flexible to permit a limited range of motion, and when oriented on the front of the knee the joint rehabilitation device pushes the knee joint into passive knee extension.

3. The joint rehabilitation device of claim 2, wherein the flat leaf spring is reconfigurable to be orientated along a back of the knee.

4. The joint rehabilitation device of claim 3, wherein, the flat leaf spring is oriented along the back of the knee, when the knee is extended, leg muscles associated with the knee are strengthened.

5. The joint rehabilitation device of claim 2, further comprising a ratcheting knob and a retractable wire configured to be drawn in or released by turning the ratcheting knob, thereby permitting the flat leaf spring to be tightened to adjust attachment to the leg.

* * * * *